United States Patent
Lehmann et al.

(10) Patent No.: US 8,805,034 B2
(45) Date of Patent: Aug. 12, 2014

(54) SELECTION OF DATASETS FROM 3D RENDERINGS FOR VIEWING

(75) Inventors: Helko Lehmann, Aachen (DE); Juergen Weese, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 1296 days.

(21) Appl. No.: 12/377,151

(22) PCT Filed: Aug. 8, 2007

(86) PCT No.: PCT/IB2007/053130
§ 371 (c)(1),
(2), (4) Date: Apr. 9, 2010

(87) PCT Pub. No.: WO2008/018029
PCT Pub. Date: Feb. 14, 2008

(65) Prior Publication Data
US 2010/0189317 A1   Jul. 29, 2010

(30) Foreign Application Priority Data
Aug. 11, 2006   (EP) .................................. 06118814

(51) Int. Cl.
*G06K 9/00*   (2006.01)

(52) U.S. Cl.
USPC .......................................... 382/128; 382/154

(58) Field of Classification Search
CPC ........ G06T 15/08; G06T 15/06; G06T 15/005
USPC ................................................ 382/128, 154
See application file for complete search history.

(56) References Cited

U.S. PATENT DOCUMENTS

| | | | |
|---|---|---|---|
| 6,556,696 B1 * | 4/2003 | Summers et al. ............. | 382/128 |
| 7,133,041 B2 * | 11/2006 | Kaufman et al. ............. | 345/419 |
| 2003/0197704 A1 | 10/2003 | Tek et al. | |
| 2004/0161138 A1 * | 8/2004 | Ashton ........................ | 382/128 |
| 2004/0252870 A1 * | 12/2004 | Reeves et al. ................ | 382/128 |
| 2005/0065424 A1 | 3/2005 | Shah et al. | |
| 2005/0078858 A1 * | 4/2005 | Yao et al. ..................... | 382/128 |
| 2005/0285854 A1 | 12/2005 | Morita et al. | |
| 2006/0033737 A1 | 2/2006 | Old et al. | |

OTHER PUBLICATIONS

D. R. Nadeau, Volume scene graphs, Proceedings of the IEEE Symposium on Volume Visualization, pp. 49-56, 2000.*

(Continued)

*Primary Examiner* — John Pauls
*Assistant Examiner* — Jonathan Durant

(57) ABSTRACT

The invention relates to a system (100) for visualizing medical image data, the system comprising: a first display unit (110) for displaying a first view of the medical image data; an indication unit (115) for indicating a location on the displayed first view; a trigger unit (120) for triggering an event; an identification unit (125) for identifying an anatomical structure comprised in the medical image data, based on the indicated location on the displayed first view, in response to the triggered event; a selection unit (130) for selecting a part of the medical image data based on the identified anatomical structure; and a second display unit (135) for displaying a second view of the selected part of the medical image data, thereby visualizing the medical image data. Thus, the system (100) allows for visualizing an anatomical structure of interest comprised in the part of the medical image data.

17 Claims, 6 Drawing Sheets

(56) References Cited

OTHER PUBLICATIONS

Kruger, Jens, and Rüdiger Westermann. "Acceleration techniques for GPU-based volume rendering." Proceedings of the 14th IEEE Visualization 2003 (VIS'03). IEEE Computer Society, 2003.*

Snel J G et al: "A Distributed Workflow Management System for Automated Medical Image Analysis and Logistics" Computer-Based Medical Systems, 2006. CBMS 2006. 19th IEEE International Symposium on Salt Lake City, UT, USA Jun. 22-23, 2006, Piscataway, NJ, USA,IEEE, Jun. 22, 2006, pp. 733-738, XP010923999 ISBN: 0-7695-2517-1.

* cited by examiner

SELECTION OF DATASETS FROM 3D RENDERINGS FOR VIEWING

FIELD OF THE INVENTION

The invention relates to the field of visualization of medical image data for diagnostic purposes and more specifically to visualization of a part of medical image data comprising an anatomical structure of interest.

BACKGROUND OF THE INVENTION

A method of visualization of medical image data is described in US 2005/0065424, entitled "Method and System for Volumetric Navigation Supporting Radiological Reading in Medical Imaging Systems", hereinafter referred to as Ref. 1. This document describes synchronized viewing of different medical image data sets in different views on different viewing applications. In particular, the document describes synchronizing a view of a three-dimensional (3D) image data set with a view of a two-dimensional (2D) image data set. In an embodiment, when a radiologist manipulates a 3D visualization application and a point in the 3D space of the patient, information is identified via a cross-hair on an image; this exact point location will be transmitted to a 2D viewing application such as a PACS system. When the PACS system receives this 3D point, it will identify the appropriate image within the base data set that contains that point, automatically navigate to that slice, display a view of that slice, and identify the same point with a cross-hair.

SUMMARY OF THE INVENTION

A deficiency of the system described in Ref. 1 is that the image data within the base data set is identified on the basis of a point in 3D space indicated by a user, such as a radiologist. The system does not allow the user to select an anatomical structure of interest for viewing. Thus, the 2D view of the image data may be suboptimal for viewing the anatomical structure of interest.

It would be advantageous to have an improved system capable of better visualizing an anatomical structure of interest comprised in medical image data.

To address this concern, in an aspect of the invention, a system for visualizing medical image data comprises:

a first display unit for displaying a first view of the medical image data;

an indication unit for indicating a location on the displayed first view;

a trigger unit for triggering an event;

an identification unit for identifying an anatomical structure comprised in the medical image data, based on the indicated location on the displayed first view, in response to the triggered event;

a selection unit for selecting a part of the medical image data based on the identified anatomical structure; and a second display unit for displaying a second view of the selected part of the medical image data, thereby visualizing the medical image data.

The first view of the medical image data is displayed by the first display unit. The first view allows a user of the system to view and to indicate an anatomical structure of interest to the user. Indicating may involve standard operations like translating, rotating, zooming-in and/or zooming-out the medical image data. The anatomical structure of interest may be the heart of a human patient. The indication unit and the trigger unit may be implemented together using a mouse device. The mouse controls the location of a pointer displayed on the display. The pointer is used for indicating a location on the displayed first view. The triggered event may be a pointer-over event. The pointer-over event is triggered when the pointer is displayed at a location of the display for a predetermined duration. The identification unit is arranged to identify the anatomical structure, e.g. the heart, shown in the view of the medical image data, based on the location of the pointer controlled by the mouse, in response to the triggered event. Based on the identified anatomical structure, the selection unit is arranged to select a part of the medical image data, e.g. a part comprising the medical image data for visualizing the identified anatomical structure. The second display unit is arranged to display a second view of the selected part of the medical image data, thereby visualizing an anatomical structure of interest comprised in the part of the medical image data.

In an embodiment of the system, the system further comprises a segmentation unit for segmenting the medical image data. Advantageously, the medical image data may be automatically, semi-automatically or manually segmented using the segmentation unit of the system. Segmentation may be used by the identification unit to identify the anatomical structure of interest to the user.

In an embodiment of the system, the medical image data is segmented and identifying the anatomical structure is based on the segmented medical image data. The medical image data may be segmented by the segmentation unit of the system. Alternatively, the system may be arranged to obtain a segmented medical image data. For example, segmentation may be based on a shape model. The shape model may comprise a surface mesh, e.g. a triangular mesh. During segmentation, the triangular mesh is adapted to the medical image data. The adapted triangular mesh is described, for example, by mesh vertex coordinates in an image data coordinate system. In this embodiment, an anatomical structure of interest may be advantageously identified based on locations comprised in a volume defined by the adapted triangular mesh.

In an embodiment of the system, the system further comprises a classification unit for classifying the medical image data. Advantageously, a data element of the medical image data may be classified using the classification unit of the system. Classification results may be used by the identification unit to identify the anatomical structure of interest to the user.

In an embodiment of the system, the medical image data is classified and identifying the anatomical structure is based on the classified medical image data. The medical image data may be classified by the classification unit of the system. Alternatively, the system may be arranged to obtain a classified medical image data. In class-based segmentation using a classifier for classifying medical image data elements, locations comprised in the medical image data are classified as locations comprised in an anatomical structure or as locations not-comprised in an anatomical structure. In this embodiment, the anatomical structure of interest may be advantageously identified based on classification of locations comprised in data elements.

In an embodiment of the system, the medical image data comprising a plurality of member image data for multi-volume rendering and identifying the anatomical structure is based on data membership of the medical image data. In this embodiment, each medical image data element is characterized by data set membership. Each member image data is assumed to describe an anatomical structure. The data elements displayed in the first view are characterized by their data membership. In this embodiment, the anatomical structure is identified based on the membership of data elements displayed in the first view.

In an embodiment of the system, the second view of the selected part of the medical image data is further based on the indicated location. The indicated location within the medical image data may provide further clues for determining an optimal second view of the selected part of the medical image data. For example, the indicated location may determine a section plane for determining a sectional view of the part of the medical image data, said section plane substantially comprising the indicated location. The plane may be perpendicular to the viewing plane of the first view.

In an embodiment of the system, the second view of the selected part of the medical image data is based on the identified anatomical structure. In an embodiment, the type of view may be determined based on a user input. In a further embodiment, the type of view may be determined by the system, based on the identified anatomical structure.

In a further aspect of the invention, an image acquisition apparatus comprises a system for visualizing medical image data, the system comprising:
    a first display unit for displaying a first view of the medical image data;
    an indication unit for indicating a location on the displayed first view;
    a trigger unit for triggering an event;
    an identification unit for identifying an anatomical structure comprised in the medical image data, based on the indicated location on the displayed first view, in response to the triggered event;
    a selection unit for selecting a part of the medical image data based on the identified anatomical structure; and
    a second display unit for displaying a second view of the selected part of the medical image data, thereby visualizing the medical image data.

In a further aspect of the invention, a workstation comprises a system for visualizing medical image data, the system comprising:
    a first display unit for displaying a first view of the medical image data;
    an indication unit for indicating a location on the displayed first view;
    a trigger unit for triggering an event;
    an identification unit for identifying an anatomical structure comprised in the medical image data, based on the indicated location on the displayed first view, in response to the triggered event;
    a selection unit for selecting a part of the medical image data based on the identified anatomical structure; and
    a second display unit for displaying a second view of the selected part of the medical image data, thereby visualizing the medical image data.

In a further aspect of the invention, a method of visualizing medical image data comprises:
    a first display step for displaying a first view of the medical image data;
    an indication step for indicating a location on the displayed first view;
    a trigger step for triggering an event;
    an identification step for identifying an anatomical structure comprised in the medical image data, based on the indicated location on the displayed first view, in response to the triggered event;
    a selection step for selecting a part of the medical image data based on the identified anatomical structure; and
    a second display step for displaying a second view of the selected part of the medical image data, thereby visualizing the medical image data.

In a further aspect of the invention, a computer program product to be loaded by a computer arrangement comprises instructions for visualizing medical image data, the computer arrangement comprising a processing unit and a memory, the computer program product, after being loaded, providing said processing unit with the capability to carry out the following tasks:
    displaying a first view of the medical image data;
    indicating a location on the displayed first view;
    triggering an event;
    identifying an anatomical structure comprised in the medical image data, based on the indicated location on the displayed first view, in response to the triggered event;
    selecting a part of the medical image data based on the identified anatomical structure; and
    displaying a second view of the selected part of the medical image data, thereby visualizing the medical image data.

Modifications and variations thereof, of the image acquisition apparatus, of the workstation, of the method, and/or of the computer program product, which correspond to modifications of the system and variations thereof being described, can be carried out by a skilled person on the basis of the present description.

The skilled person will appreciate that the method may be applied to volumetric, i.e. three-dimensional (3D), image data acquired by various acquisition modalities such as, but not limited to, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

The same reference numerals are used to denote similar parts throughout the Figures.

DETAILED DESCRIPTION OF EMBODIMENTS

Figure 1:
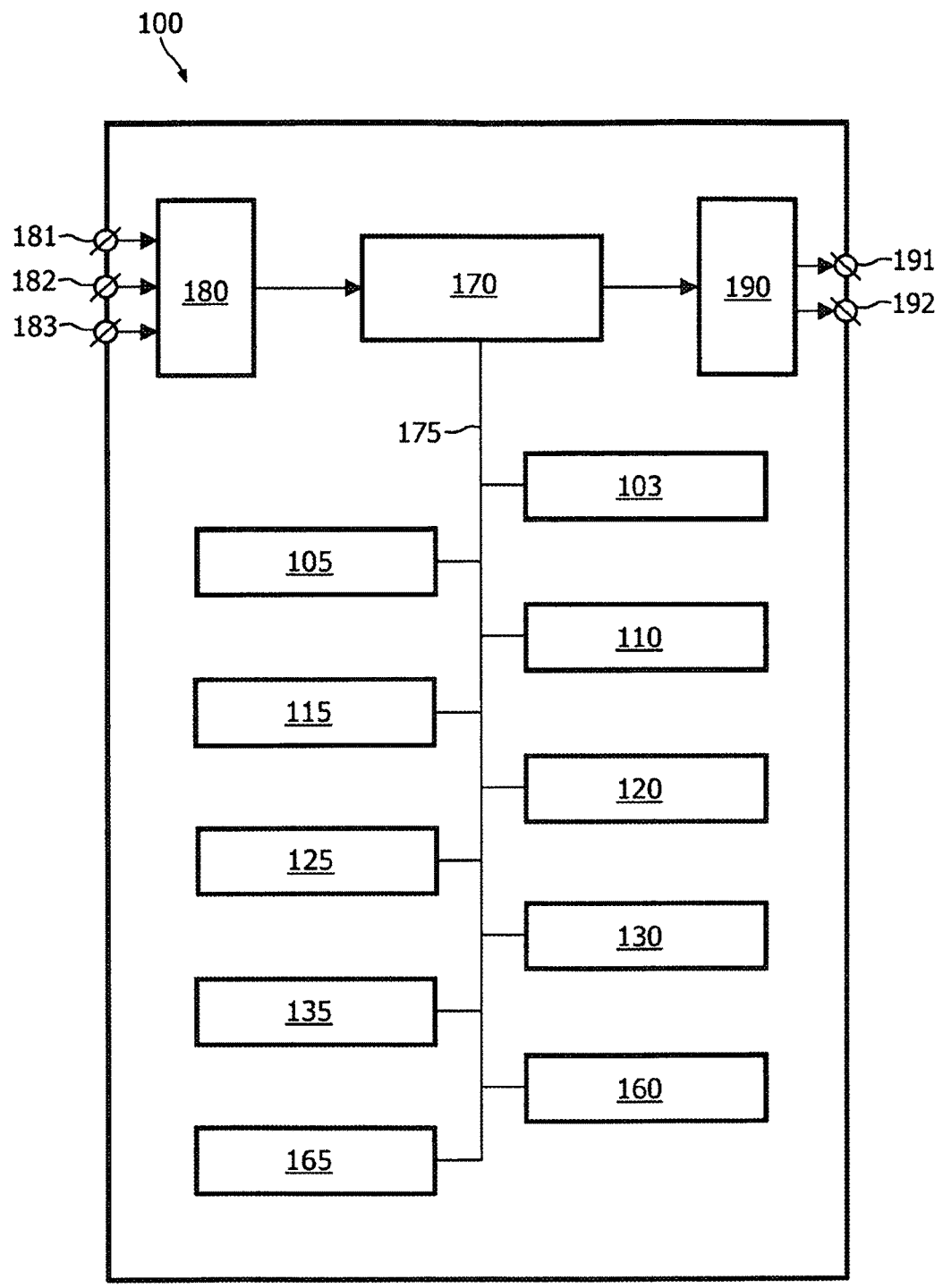
FIG. 1 schematically shows a block diagram of an exemplary embodiment of the system.

FIG. 1 schematically shows a block diagram of an exemplary embodiment of the system 100 for visualizing medical image data, the system 100 comprising:
    a first display unit 110 for displaying a first view of the medical image data;
    an indication unit 115 for indicating a location on the displayed first view;
    a trigger unit 120 for triggering an event;

an identification unit 125 for identifying an anatomical structure comprised in the medical image data, based on the indicated location on the displayed first view, in response to the triggered event;

a selection unit 130 for selecting a part of the medical image data based on the identified anatomical structure; and a second display unit 135 for displaying a second view of the selected part of the medical image data, thereby visualizing the medical image data.

The exemplary embodiment of the system 100 further comprises the following units:

a segmentation unit 103 for segmenting the medical image data;

a classification unit 105 for classifying the medical image data;

a control unit 160 for controlling the workflow in the system 100;

a user interface 165 for communicating with a user of the system 100; and a memory unit 170 for storing data.

In the exemplary embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device, such as a keyboard. The input connectors 181, 182 and 183 are connected to an input control unit 180.

In the exemplary embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 of the system 100 and output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analogue telephone network.

In the exemplary embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, the medical image data. The memory unit 170 may be embodied by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the selected part of the medical image data and/or a log file documenting the use of the system 100. The memory unit 170 is also arranged to receive data from and deliver data to the units of the system 100 comprising the segmentation unit 103, the classification unit 105, the first display unit 110, the indication unit 115, the trigger unit 120, the identification unit 125, the selection unit 130, the second display unit 135, the control unit 160, and the user interface 165, via a memory bus 175. The memory unit 170 is further arranged to make the output data available to external devices via any of the output connectors 191 and 192. Storing the data from the units of the system 100 in the memory unit 170 may advantageously improve the performance of the units of the system 100 as well as the rate of transfer of the output data from the units of the system 100 to external devices.

Alternatively, the system 100 may not comprise the memory unit 170 and the memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In the exemplary embodiment of the system 100 shown in FIG. 1, the system 100 comprises a control unit 160 for controlling the workflow in the system 100. The control unit may be arranged to receive control data from and provide control data to the units of the system 100. For example, after an event has been triggered by the trigger unit 110, the trigger unit 110 may be arranged to pass a control data "event triggered" to the control unit 160 and the control unit 160 may be arranged to provide a control data "identify the anatomical structure" to the identification unit 125, requesting the identification unit 125 to identify the anatomical structure based on the indicated location. Alternatively, a control function may be implemented in another unit of the system 100.

In the exemplary embodiment of the system 100 shown in FIG. 1, the system 100 comprises a user interface 165 for communicating with the user of the system 100. The user interface 165 may be arranged to provide the user with means for rotating and translating the medical image data viewed on the display. Optionally, the user interface may receive a user input for selecting a mode of operation of the system 100, such as a mode for using the segmentation unit 103 for segmenting the medical image data. The skilled person will understand that more functions may be advantageously implemented in the user interface 165 of the system 100.

Volumetric, i.e. three-dimensional (3D), medical image data comprises elements. Each data element (x, y, z, I) of the medical image data comprises a location (x, y, z), typically represented by three Cartesian coordinates x, y, z in an image data coordinate system, and an intensity I at this location. The medical image data volume may be defined as a volume comprising all locations (x, y, z) comprised in the image data elements (x, y, z, I). When the medical image data comprises a plurality of member image data, each data element may further comprise an image data membership index m. Member image data may be obtained in many different ways. For example, a first member image data may be acquired using a first image data acquisition modality and a second member image data may be acquired using a second image data modality. Alternatively, member image data may be obtained by processing medical image data, for example, by segmenting the medical image data and partitioning the medical image data into a plurality of member image data based on the segmentation. The skilled person will understand that the way in which a member image data is obtained does not limit the scope of the claims.

The first display unit 110 of the system 100 is arranged to display a view of the medical image data on a display. The view may be computed using, for example, maximum intensity projections (MIP), iso-surface projection (ISP), direct volume rendering (DVR), and/or digitally recomputed radiographs (DRR). In MIP, a pixel on the display is set to the maximum value along a projection ray. In ISP, projection rays are terminated when they hit the iso-surface of interest. The iso-surface is defined as the level set of the intensity function, i.e. as the set of all voxels having the same intensity. More information on MIP and ISP can be found in a book by Barthold Lichtenbelt, Randy Crane, and Shaz Naqvi, entitled "Introduction to Volume Rendering", published by Hewlett-Packard Professional Books, Prentice Hall; Bk&CD-Rom edition (1998). In DVR, a transfer function assigns a renderable property such as opacity to intensities comprised in the medical image data. An implementation of DVR is described in an article by T. He et al entitled "Generation of Transfer Functions with Stochastic Search Techniques" in Proceedings of IEEE Visualization, pages 227-234, 1996. In DRR, a projection image, e.g. an X-ray image, is reconstructed from volumetric data, e.g. from CT data. An implementation of DRR is described in an article by J. Alakijala et al entitled "Reconstructing of digital radiographs by texture mapping, ray casting and splatting" in Engineering in Medicine and Biology, 1996, Bridging Disciplines for Biomedicine, Proceedings of the 18$^{th}$ Annual International Conference of the IEEE, vol. 2, pages 643-645, 1996. The skilled person will understand that there are many methods that may be employed for computing the view of medical image data. The choice of a method of computing the first view of medical image data docs not limit the scope of the claims.

In multi-volume visualization, the displayed image is determined based on a plurality of member image data. A few data elements belonging to different member image data may correspond to one location. A method of multi-volume DVR is described in an article by D. R. Nadeau entitled "Volume scene graphs", published in Proceedings of the IEEE Symposium on Volume Visualization, pages 49-56, 2000.

In an embodiment of the system 100, the system 100 further comprises the segmentation unit 103 for segmenting the medical image data. The medical image data may be automatically, semi-automatically, and/or manually segmented using the segmentation unit 103 of the system 100. The skilled person will understand that there are many candidate segmentation systems and that a good candidate segmentation system may be integrated as a segmentation unit 103 of the system 100.

In an embodiment of the system 100, the system 100 further comprises a classification unit 105 for classifying the medical image data. A data element of the medical image data may be classified using the classification unit 105 of the system 100. The skilled person will understand that there are many candidate classification systems and that a good candidate classification system may be integrated as a classification unit 105 of the system 100.

The indication unit 115 of the system 100 is arranged to indicate a location on the displayed view. The location on the displayed view is used by the identification unit 125 for identifying an anatomical structure which is of interest to the user. In an embodiment of the system 100, the indication unit 115 may be implemented using a mouse device, i.e. the user may control a pointer indicating a location on a display by using the mouse. Alternatively, the pointer may be controlled using a trackball or using a keyboard. The pointer may be replaced by another tool, e.g. by a horizontal and a vertical crosshair. The horizontal and the vertical crosshair may be controlled by a mouse or otherwise. The skilled person will understand that the method employed for indicating the location on the displayed view does not limit the scope of the claims.

The trigger unit 120 of the system 100 is arranged to trigger an event. The event triggered by the trigger unit 120 is used by the identification unit 125 to begin identifying an anatomical structure. The triggered event further triggers the selection unit 130 to select a part of the medical image data based on the identified anatomical structure. The triggered event further triggers the second display unit for displaying a second view of the part of the segmented image data. In an embodiment of the system 100, the trigger unit 120 may be implemented together with the indication unit 115 as a mouse device. The trigger unit 120 may be arranged to trigger one event, e.g. a pointer-over event or a pointer-over-and-click event implemented by the mouse device. The pointer-over event may be arranged to occur when the pointer controlled by the mouse stops at a location on the display for a predetermined period of time, e.g. for 1 second. The pointer-over-and-click event may be arranged to occur when the pointer is at a location on the display and a mouse button is clicked. The skilled person will know other events and other ways to implement events. The exemplary embodiments of the trigger unit 120 of the system are for illustrating the invention and should not be construed as limiting the scope of the claims.

The identification unit 125 is arranged to identify an anatomical structure comprised in the medical image data, based on the indicated location on the displayed first view, in response to the triggered event. The anatomical structure visualized at the indicated location is the identified anatomical structure. In one embodiment, the anatomical structure is determined based on a probing ray starting substantially at the indicated location on the display, i.e. in the viewing plane, and propagating in a direction substantially perpendicular to the display into the visualized volume of the medical image data. For example, the identification unit 125 may be arranged to probe the medical image data at equidistant locations along the probing ray. At each of the equidistant locations on the probing ray, the nearest data element is obtained from the medical image data. In the case of ISP, the intensity of the nearest data element is compared to an intensity threshold of the ISP. The anatomical structure which comprises the location of the first data element with an intensity greater than the intensity threshold, is the identified anatomical structure. Similarly, for MIP, the detected data element is the first data element with the highest intensity along the probing ray. The anatomical structure which comprises the location of the first data element with the highest intensity along the probing ray, is the identified anatomical structure. Similarly, in multi-volume visualization of a plurality of member image data employing DVR, an element along the probing ray is selected based on the opacity, or an alternative renderable property, assigned to the intensities of elements along the probing ray. When an element with an opacity larger than or equal to an opacity threshold is found, the membership index of this element determines the member image data and hence the anatomical structure.

There are many possible embodiments of the identification unit 125 of the system 100. In an embodiment of the system 100, the medical image data is segmented and identifying the anatomical structure is based on the segmented medical image data. For example, medical image data describing a heart may comprise anatomical structures such as left ventricle, right ventricle, left atrium, right atrium, myocardium around the left ventricle, main trunks of the coronary arteries, ostia, and valves, for example. Segmentation may be achieved using different methods and tools comprising, but not limited to, adapting rigid, scalable, or elastically deformable models to the medical image data, using classifiers (so-called voxel classifiers) for classifying data elements of the medical image data, and classifying a data element of the medical image data based on image data membership in a multi-volume visualization. The segmented medical image data comprises the medical image data and the segmentation results.

In an embodiment of the system 100, the segmentation results comprise coordinates of vertices of adapted model meshes in the image data coordinate system. The model mesh is adapted to an anatomical structure. The model mesh describes the surface of the anatomical structure to which it is adapted. Image segmentation based on adapting surface model meshes to anatomical structures in medical image data is described in an article by H. Delingette entitled "General Object Reconstruction based on Simplex Meshes" in International Journal of Computer Vision, vol. 32, pages 11-142, 1999.

In an embodiment of the system 100, the medical image data is segmented, and identifying the anatomical structure is based on the segmented medical image data. Each adapted model mesh determines an anatomical structure volume bounded by the surface of the adapted mesh. The volume of the anatomical structure comprising the detected data element determines the identified anatomical structure.

The medical image data may be segmented by the segmentation unit 103. In one embodiment, the entire medical image data is segmented. Optionally, the segmentation may be performed locally at the location comprised in the first data element, along the probing ray. Alternatively, the medical image data obtained by the system 100 is segmented.

In an embodiment of the system 100, the medical image data is classified, and identifying the anatomical structure is based on the classified medical image data. The classification is based on a feature of the data element and/or on a feature of neighboring data elements. For example, the feature of the data element may be intensity comprised in the data element and the feature of the nearby elements may be a pattern comprised in the nearby elements. Data elements assigned to one class define one anatomical structure. The class of data elements defining the anatomical structure is hereinafter referred to as the class associated with the anatomical structure. Classification may be also applied to voxels. A voxel comprises a small volume of the image volume and intensity assigned to the small volume. The skilled person will understand that a voxel may be considered an equivalent of an image data element. Magnetic Resonance (MR) brain image data segmentation based on classification of data elements in a MR brain image data is described in an article by C. A. Cocosco et al entitled "A Fully Automatic and Robust Brain MRI Tissue Classification Method" in Medical Image Analysis, vol. 7, pages 513-527, 2003.

The identified anatomical structure comprised in the medical image data is based on the class assigned to the detected data element. The anatomical structure associated with the class of the data element detected along the probing ray defines the identified anatomical structure. Classification of the first data element detected along the probing ray may be carried out by the classification unit after detection or prior to detection. Alternatively, the medical image data obtained by the system 100 are classified.

In an embodiment of the system 100, the medical image data comprises a plurality of member image data for multi-volume rendering, and identifying the anatomical structure is based on data membership of the medical image data. All structures comprised in a member image data are assumed to define one anatomical structure associated with the member image data. The membership index of the data element detected along the probing ray defines the identified anatomical structure.

The skilled person will appreciate that it is possible to combine a few embodiments of the system 100. For example, it is possible that a member image data is further segmented and/or classified. The identification unit 125 may be arranged to identify an anatomical structure comprised in the segmented and/or classified member image data. The selection unit 130 may be arranged to select a part of the member image data, based on the identified anatomical structure, for displaying the second view.

The skilled person will understand that the medical image data may describe various anatomical structures, for example, cardiac structures, lung structures, colon structures, structures of an artery tree, structures of the brain, etc.

If the identification unit 125 fails to identify the anatomical structure based on the location indicated on the display by the indication unit 115, then the control unit 160 may be arranged to execute a default "failed" action, e.g. the control unit may request the user interface to display a message "no anatomical structure is associated with the indicated location".

The described methods for identifying the anatomical structure comprised in the medical image data illustrate embodiments of the identification unit 125. The scope of the claims does not depend on the method of identifying the anatomical structure comprised in the medical image data employed by the identification unit 125.

The selection unit 130 of the system 100 is arranged to select a part of the medical image data based on the identified anatomical structure. Once the anatomical structure is identified, the selected part of the medical image data may be defined as a set comprising data elements of the anatomical structure or of a part thereof.

In an embodiment of the system 100, the selected part of the medical image data is based on a shape model of the identified anatomical structure. In this embodiment, the selected part of the medical image data may be determined based on locations comprised in a volume bounded by the adapted mesh of the shape model.

In an embodiment of the system 100, the selected part of the medical image data is based on a class of the identified anatomical structure. The selected part of the medical image data may be advantageously determined based on locations classified as locations comprised in the identified anatomical structure.

In an embodiment of the system 100, the selected part of the medical image data is based on a member image data comprising the anatomical structure. The selected part of the medical image data may be determined based on the member image data comprising the identified anatomical structure.

The second display unit 135 of the system 100 is arranged to display a second view of the selected part of the medical image data. The second view may visualize the selected anatomical structure or a part thereof. For example, the second view may show a sectional view of the selected anatomical structure. Alternatively, the second view may show a 3D view of the selected anatomical structure. The skilled person will understand that displaying a plurality of views, e.g. a plurality of sectional views, based on the selected anatomical structure is also contemplated.

In an embodiment of the system 100, the second view of the selected part of the medical image data is based on the identified anatomical structure. For example, the second display unit 135 may be arranged to compute the three mutually orthogonal principal axes of an inertia tensor of the selected anatomical structure. The three mutually orthogonal principal axes of the inertia tensor may be used for determining three mutually orthogonal section planes. The second display unit may be further arranged to display three sectional views of the selected anatomical structure using the three section planes.

The second view of the selected part of the medical image data is based on the identified anatomical structure. For example, the first view may visualize the ostium of a coronary, i.e. where the coronary leaves the aorta. A stenosis at this point is extremely dangerous. To check for a stenosis at this location, a view must be generated, where the aorta does not hide the ostium of the coronary, for example, where the ostium is visible on one side of the aorta. Similar views may be generated for the locations where the renal arteries supplying the kidneys leave the aorta. In a further embodiment, when clicking on the left ventricle, for instance, a short-axis view of the ventricle is generated. In an embodiment, the type of view may be determined based on a user input. In a further embodiment, the type of view may be determined by the system based on the identified anatomical structure.

Figure 2:
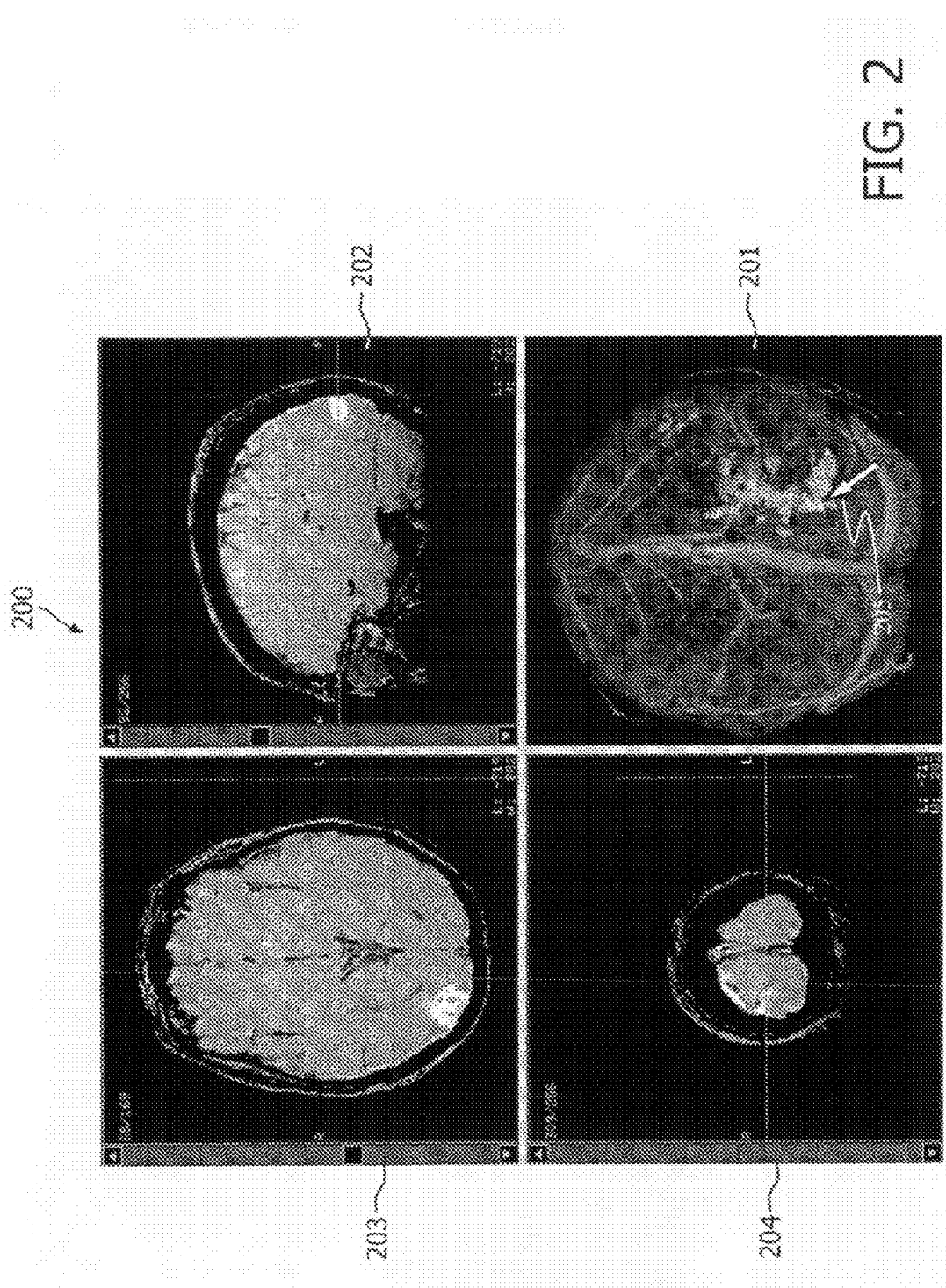
FIG. 2 illustrates indicating a first location in the first view displayed by the system.
Figure 3:
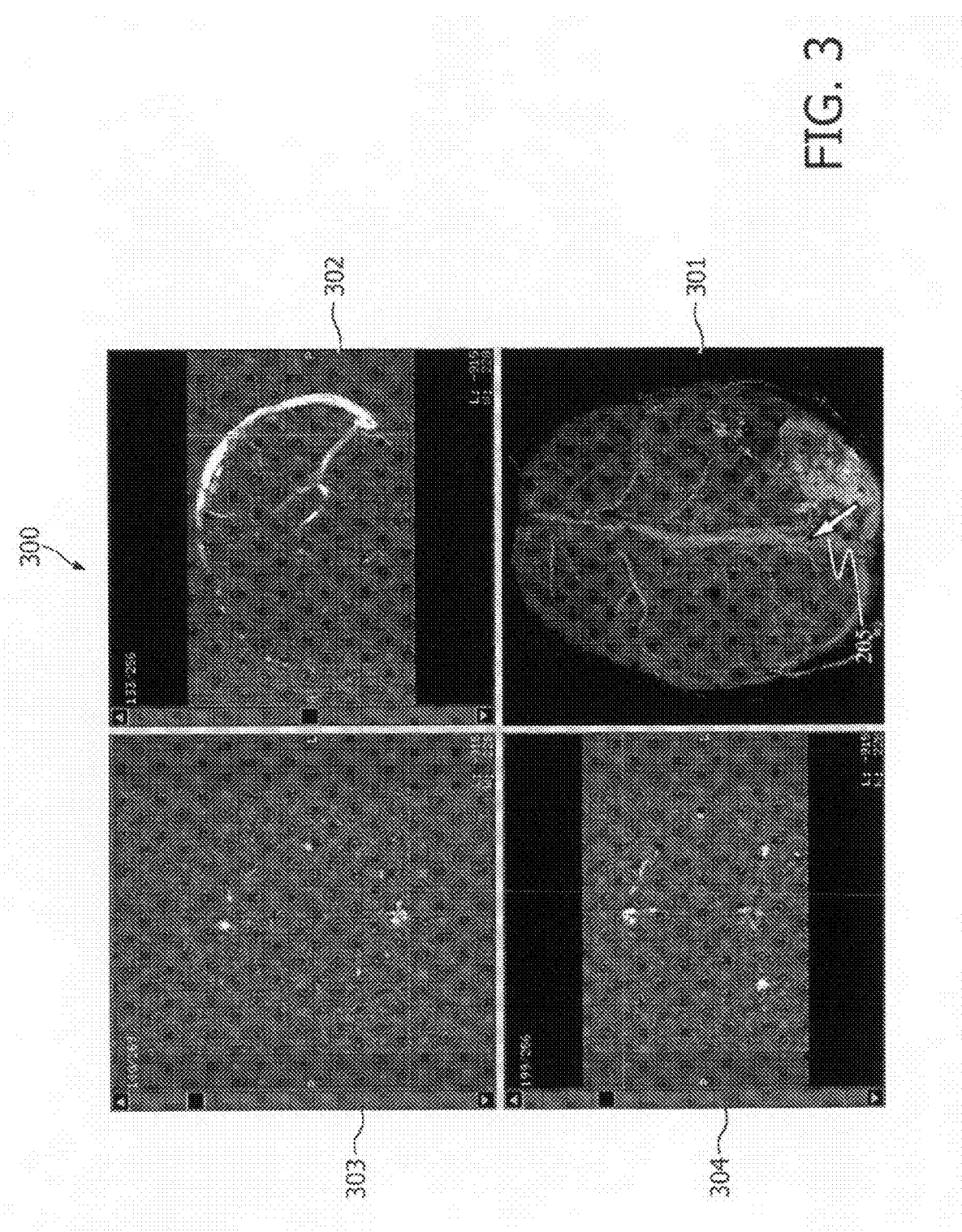
FIG. 3 illustrates indicating a second location in the first view displayed by the system.

FIGS. 2 and 3 show an embodiment of the system 100: a magnetic resonance (MR) neurological application package typically used for stroke assessment, surgical planning, or for therapy monitoring. The medical image data comprises two member image data. The first member image data comprises T1 MR data for visualizing brain tissue. The second member image data comprises MR angiography for visualizing vessel tissue.

FIG. 2 illustrates indicating a first location in the first view displayed by the system 100. In FIG. 2, a location in brain tissue is indicated by a pointer 205. A displayed image 200 comprises four viewports. In the bottom-right viewport 201, the first view of the medical image data is rendered using multi-volume DVR. The pointer 205 indicates a location in the bottom-right viewport 201 displaying the first view. Based on the location of the pointer, the identification unit 125 is arranged to identify the anatomical structure of interest to the user, i.e. the member image data. The medical image data is probed using a probing ray starting substantially at the indicated location in the viewing plane of the first view and propagating in a direction substantially perpendicular to the viewing plane into the visualized volume of the medical image data. A plurality of probing locations on the probing ray is generated. At each probing location on the probing ray, a data element nearest to that location is obtained from each of the member image data. The image intensity of the two data elements is converted into opacity values, using a DVR transfer function. If the opacity value corresponding to one of the data elements is greater than or equal to an opacity threshold, the data element membership index is identified. The membership index m of this data element determines the member image data and the anatomical structure comprised in this member image data.

In FIG. 2 the anatomical structure identified on the basis of the indicated location is brain tissue comprising tumor tissue. This brain tissue comprising tumor tissue is visualized by the second display unit 135 in three sectional views of the brain tissue shown in the top-right viewport 202, in the top-left viewport 203, and in the bottom-left viewport 204.

FIG. 3 illustrates indicating a second location in the first view displayed by the system 100. In FIG. 3, a location in vessel tissue is indicated by a pointer 305. A displayed image 300 comprises four viewports. In the bottom-right viewport 301, the first view of the medical image data is rendered using multi-volume DVR. The pointer 305 indicates a location in the bottom-right viewport 301 displaying the first view. Based on the location of the pointer, the identification unit 125 is arranged to identify the anatomical structure of interest to the user, i.e. the member image data, using the identification method described in the description of FIG. 2.

In FIG. 3, the anatomical structure identified on the basis of the indicated location is vessel tissue comprised in the second member image data comprising MR angiography data. Thus, the vessel tissue comprised in the second member image data is displayed by the second display unit 135 in three sectional views shown in the top-right viewport 302, in the top-left viewport 303, and in the bottom-left viewport 304.

In an embodiment of the system 100, the second view of the selected part of the medical image data is further based on the indicated location. The indicated location allows determining a 3D location within the medical image data. The 3D location may provide further clues for determining an optimal second view of the selected part of the medical image data. For example, the indicated location may determine a section plane for determining a sectional view of the part of the medical image data, which section plane substantially comprises the indicated location. The plane may be perpendicular to the viewing plane of the first view. Optionally, the 3D location may be a center of origin of a Cartesian system of coordinates for determining three substantially mutually orthogonal sectional views of the selected anatomical structure.

The skilled person will understand that the system 100 described in the current document may be a valuable tool for assisting a physician in medical diagnosing, in particular in interpreting and extracting information from medical image data.

The skilled person will further understand that other embodiments of the system 100 are also possible. It is possible, among other things, to redefine the units of the system and to redistribute their functions. For example, in an embodiment of the system 100, the functions of the indication unit 115 may be combined with the functions of the first trigger unit 120. In a further embodiment of the system 100, there can be a plurality of segmentation units replacing the segmentation unit 103. Each segmentation unit from the plurality of segmentation units may be arranged to employ a different segmentation method. The method employed by the system 100 may be based on a user selection.

The units of the system 100 may be implemented using a processor. Normally, their functions are performed under the control of a software program product. During execution, the software program product is normally loaded into a memory, like a RAM, and executed from there. The program may be loaded from a background memory, like a ROM, hard disk, or magnetic and/or optical storage means, or may be loaded via a network like the Internet. Optionally, an application-specific integrated circuit may provide the described functionality.

Figure 4:
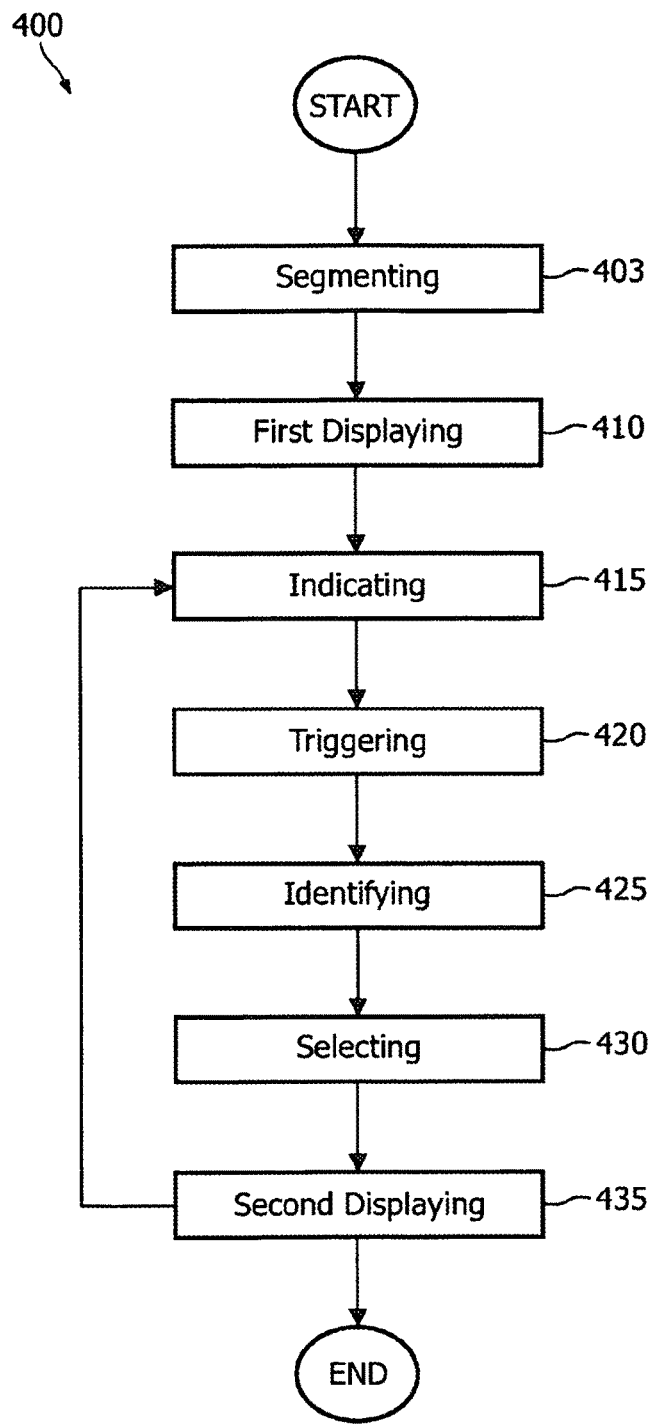
FIG. 4 shows a flowchart of an exemplary implementation of the method.

FIG. 4 shows a flowchart of an exemplary implementation of the method 400 of visualizing medical image data. The method 400 begins with a segmentation step 403 for segmenting the medical image data. After segmenting the medical image data, the method 400 continues to a first display step 410 for displaying a view of the medical image data on a display. After the first display step 410, the method continues to an indication step 415 for indicating a location on the displayed view. Then the method 400 continues to a trigger step 420 for triggering an event. The next step is an identification step 425 for identifying an anatomical structure comprised in the medical image data, based on the indicated location on the displayed first view, in response to the triggered event. After the identification step 425, the method 400 continues to a selection step 430 for selecting a part of the medical image data based on the identified anatomical structure. After the selection step 425, the method 400 continues to a second display step 430 for displaying a second view of the selected part of the medical image data. After the second display step 435, the method 400 may terminate. Alternatively, the method 400 may continue to the indication step 415.

The segmentation step 403 may be carried out separately from other steps, at another time and place. Alternatively, the segmentation step may be replaced by a classification step for classifying the medical image data or may be omitted, e.g. in the case of multi-volume rendering.

The order of steps in the method 400 is not mandatory; the skilled person may change the order of some steps or perform some steps concurrently using threading models, multi-processor systems or multiple processes without departing from the concept as intended by the present invention. Optionally, two or more steps of the method 400 of the current invention may be combined into one step. Optionally, a step of the method 400 of the current invention may be split into a plurality of steps.

Figure 5:
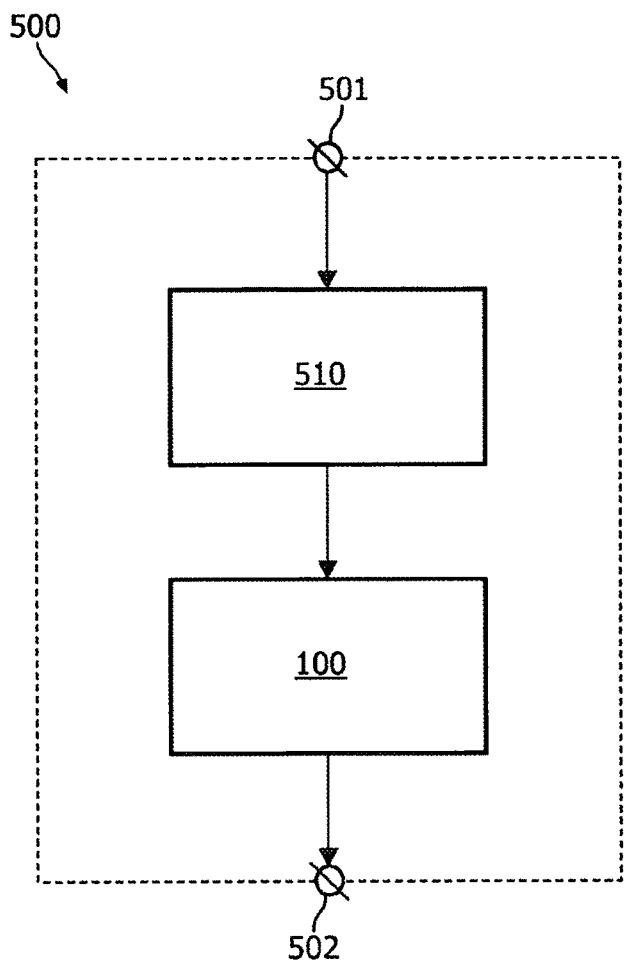
FIG. 5 schematically shows an exemplary embodiment of the image acquisition apparatus.

FIG. 5 schematically shows an exemplary embodiment of the image acquisition apparatus 500 employing the system 100, said image acquisition apparatus 500 comprising an image acquisition unit 510 connected via an internal connection with the system 100, an input connector 501, and an output connector 502. This arrangement advantageously increases the capabilities of the image acquisition apparatus 500, providing said image acquisition apparatus 500 with advantageous capabilities of the system 100 for visualizing medical image data. Examples of image acquisition apparatus comprise, but are not limited to, a CT system, an X-ray system, an MRI system, an US system, a PET system, a SPECT system, and an NM system.

Figure 6:
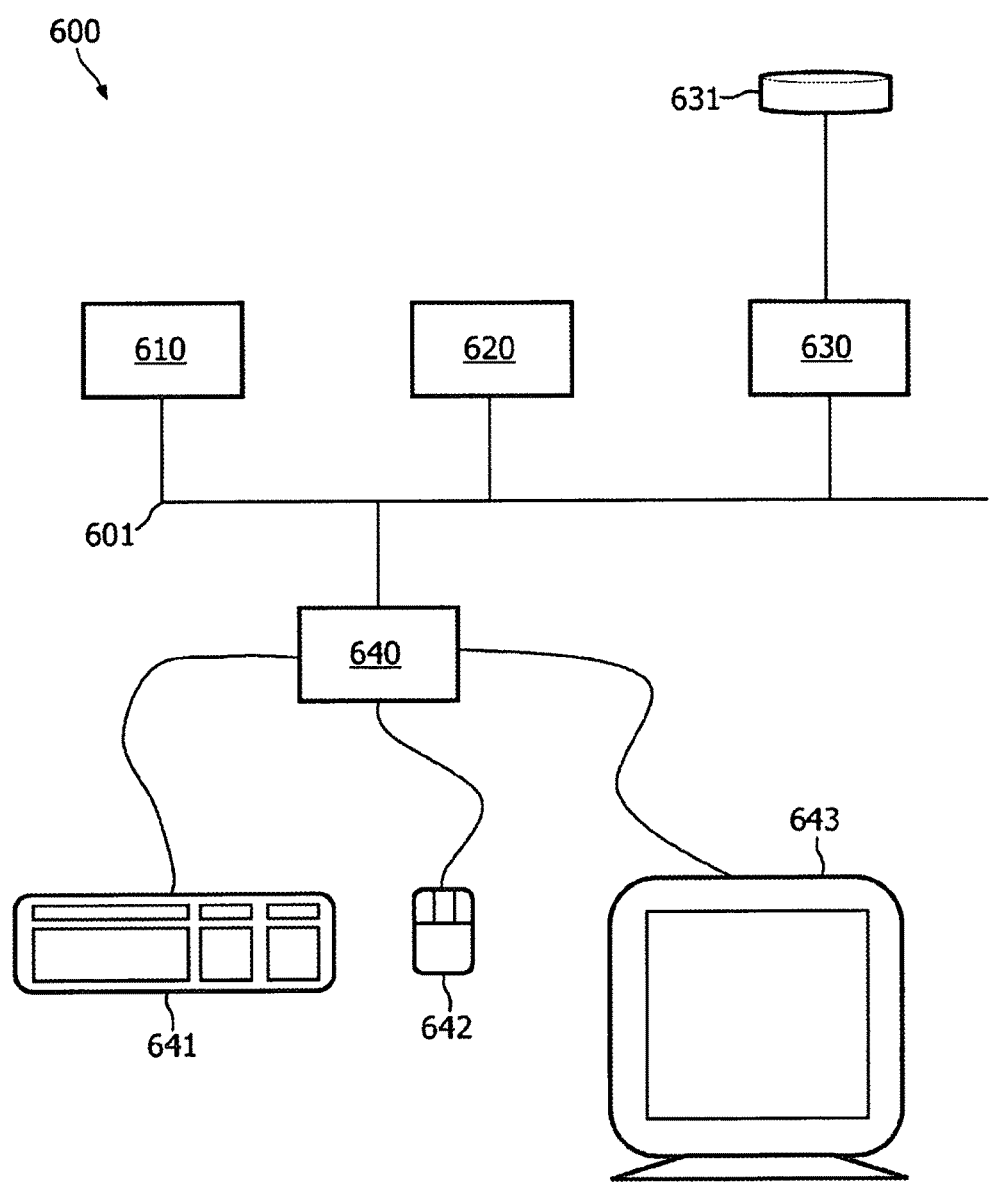
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600 using the keyboard 641 and/or the mouse 642. The workstation is arranged to output information to the display device 643 and/or to the disk 631. The skilled person will understand that there are numerous other embodiments of the workstation 600 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, et cetera does not indicate any ordering. These words are to be interpreted as names.

The invention claimed is:

1. A system having one or more processors for visualizing medical image data comprising a plurality of member image data, each having a data element membership index, for multi-volume rendering, the system comprising one or more computer processors configured to:
control one or more display devices to display a first view of the medical image data on a viewing plane based on the plurality of member image data, wherein the first view shows first member image data obtained through a first modality;
indicate a location on the first view displayed on the viewing plane;
trigger propagation of a probing ray from the indicated location perpendicular to the viewing plane into the first medical image data;
identify an anatomical structure in the first medical image data, based on the indicated location on the displayed first view and based on the data element membership index of the first medical image data, in response to the triggered event, locating a plurality of probing locations along the probing ray which probing ray locations correspond to data elements having an intensity obtained from the first member image data;
select a part of the first medical image data comprising the identified anatomical structure, and converting the intensities of the data elements of the identified anatomical structure into opacity values through is direct volume rendering transfer function and comparing the opacity values to an opacity threshold, and if the opacity threshold is exceeded, identifying the data element membership index to select the part of the first member image data and the anatomical structure of the data element; and
control the one or more display devices to display a second view of the selected part of the medical image data, wherein the selected part of the medical image data is based on a second set of member image data of the plurality of member image data comprising the identified anatomical structure obtained through a second modality, thereby visualizing the medical image data wherein the second view of the selected part of the medical image data is further based on the indicated location and the identified anatomical structure.

2. The system as claimed in claim 1, wherein the one or more processors are configured to segment the medical image data.

3. The system as claimed in claim 2, wherein the one or more processors are further configured to identify the anatomical structure based on the segmented medical image data.

4. The system as claimed in claim 1, wherein the one or more processors are further configured to classify the medical image data.

5. The system as claimed in claim 4, wherein the one or more processors are further configured to identify the anatomical structure is based on the classified medical image data.

6. The system as claimed in claim 1, wherein said system is contained in an image acquisition apparatus or a workstation.

7. The system as claimed in claim 1, wherein the second view displays a sectional view of the selected anatomical structure.

8. The system as claimed in claim 1, wherein the second view displays a 3D view of the selected anatomical structure.

9. The system as claimed in claim 1, wherein the probing locations are equidistant along the probing ray and retrieves the nearest member data element to each probing location.

10. The system as claimed in claim 1, wherein the second view is based on the indicated location.

11. The system as claimed in claim 10, wherein the second view is based on the indicated location through determining a section plane for the indicated location that substantially comprises the indicated location, and selecting a plane perpendicular to the viewing plane of the first view.

12. The system as claimed in claim 10, wherein the second view is centers the indicated location as a center of a constructed Cartesian coordinate system and determining three substantially mutually orthogonal sectional views of the selected anatomical structure.

13. A method of visualizing medical image data, the method comprising:

with one or more processors, controlling a first display to display a 3D first view of the medical image data using medical image data obtained through a first modality depicting an anatomical region;

with a user input device, indicating a location on the displayed 3D first view from a viewing plane and generating a triggering event;

in response to the triggering event, propagating a probing ray in a direction perpendicular to the viewing plane into the visualized medical image data, indicating at least one probing location along the probing ray, each of the probing locations corresponding to a data element having an intensity obtained from the member image data;

with the one or more processors in response to the triggering event, segmenting an anatomical structure in the anatomical region which is disposed at the indication probing location;

identifying the segmented anatomical structure based on a shape of the segmented anatomical structure;

with the one or more processors, selecting a part of the medical image data and a type of view based on the identified anatomical structure, converting the intensities of data elements into opacity values through a direct volume rendering transfer function and comparing the opacity values with an opacity threshold;

based on the comparison with the opacity threshold, identifying data element membership indices to determine the member image data and the anatomical structure of the data element; and with the one or more processors, controlling a second display to display a second view of the selected part of medical image data obtained through a second modality in the selected type of view, thereby visualizing the second modality medical image data.

14. A non-transitory computer readable medium carrying computer instructions causing one or more processors to:

cause a 3D first view of the medical image data using medical image data obtained through a first modality depicting an anatomical region to be displayed;

in response to an input from a user input device, indicate a location on the displayed 3D first view from a viewing plane and generating a triggering event;

in response to the triggering event, propagate a probing ray in a direction perpendicular to the viewing plane into the visualized medical image data, indicating at least one probing location along the probing ray, each of the probing locations corresponding to a data element having an intensity obtained from the member image data;

in response to the triggering event, segment an anatomical structure in the anatomical region which is disposed at the indication probing location;

identify the segmented anatomical structure based on a shape of the segmented anatomical structure;

select a part of the medical image data and a type of view based on the identified anatomical structure;

convert the intensities of data elements into opacity values through a direct volume rendering transfer function and comparing the opacity values with an opacity threshold;

based on the comparison with the opacity threshold, identify data element membership indices to determine the member image data and the anatomical structure of the data element; and cause a second view of the selected part of medical image data obtained through a second modality in the selected type of view to be displayed, thereby visualizing the second modality medical image data.

15. A system for visualizing medical image data, the system comprising:

a first display configured to display medical images in a viewing plane of an anatomical region of a patient;

a user input device configured to indicate a location in the medical images of the anatomical region displayed on the first display;

a second display configured to display images of a selected anatomical structure in the anatomical region; and one or more processors configured to:

receive a signal from the user input device identifying a selected anatomical structure with a probing ray starting from the indicated location on the displayed 3D first view and propagating in a direction perpendicular to the viewing plane into the visualized medical image data, indicating a plurality of probing locations along the probing ray which corresponds to data elements having intensities obtained from the member image data, segment the selected anatomical structure, from the segmented anatomical structure, generate an identification of the anatomical structure, the intensities of data elements are converted into opacity values through a direct volume rendering transfer function and compared to an opacity threshold, if the opacity threshold is exceeded, a data element membership index is identified to determine the anatomical structure of the data element, select image views of segmented anatomical structure based on the identified data element membership index and the indicated location; and control the second display to display the selected image views.

16. The system as claimed in claim 15, wherein generating the identification of the anatomical structure includes:

comparing a shape of the segmented anatomical structure with shape models.

17. The system as claimed in claim 15, wherein segmenting the anatomical structure includes:

classifying an image element at the indicated location and neighboring image elements based on features of the image elements.

* * * * *